United States Patent [19]

Giani

[11] Patent Number: 5,087,698

[45] Date of Patent: Feb. 11, 1992

[54] PROCESS FOR THE OPTICAL RESOLUTION OF DROPOPIZINE

[75] Inventor: Roberto Giani, Milan, Italy

[73] Assignee: Dompe' Farmaceutici S.p.A., Milan, Italy

[21] Appl. No.: 553,796

[22] Filed: Jul. 19, 1990

[30] Foreign Application Priority Data

Jul. 20, 1989 [IT] Italy .................. 21244 A/89

[51] Int. Cl.$^5$ .......................... C07D 295/08
[52] U.S. Cl. ........................... 544/394
[58] Field of Search ........................ 544/394

[56] References Cited

U.S. PATENT DOCUMENTS

| 4,255,426 | 3/1987 | Kraska | 544/394 |
| 4,312,877 | 1/1982 | Kraska | 544/594 |
| 4,372,958 | 2/1983 | Pestellini et al. | 544/394 |

FOREIGN PATENT DOCUMENTS

| 348713 | 1/1990 | European Pat. Off. | 544/394 |
| 349066 | 1/1990 | European Pat. Off. | 544/394 |
| 1534651 | 8/1968 | France | 544/394 |
| 2634765 | 2/1990 | France | 544/394 |

OTHER PUBLICATIONS

Henry Gilman et al., Organic Chemistry, An advanced Treatise, vol. I, pp. 256-257, (2nd edition).
Holy et al., Chem. Abst. 101-211655j (1984).
Holy et al., Chem. Abst. 103-6667q (1985).
Drabikowska et al., Chem. Abst. 107-129717w (1987).
Pitre et al., Chem. Abst. 113-5637z (1990).
Van Iersel et al., Chem. Abst. 113-6376a (1990).
Holy et al., Chem. Abst. 113-59544k (1990).
Votruba et al., Chem. Abst. 113-78694a (1990).

*Primary Examiner*—Cecilia Shen
*Attorney, Agent, or Firm*—Griffin, Branigan & Butler

[57] ABSTRACT

A process for the optical resolution of racemic dropopizine, carried out using L(+)tartaric acid as the optical resolution agent in aqueous medium, is described.

6 Claims, No Drawings

PROCESS FOR THE OPTICAL RESOLUTION OF DROPOPIZINE

The present invention relates to a process for optical resolution of dropopizine.

Dropopizine or 3-(4-phenyl-1-piperazinyl)-1,2-propanediol, has the following formula (I)

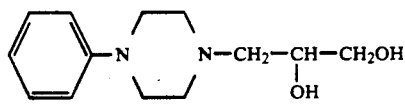

wherein the carbon atom marked with an asterisc is an asymmetrical carbon atom.

Dropopizine, in form of racemic mixture, is widely employed as antitussive agent (see Belgian patent specification no. 601394).

Optical isomers of dropopizine, the levo- and dextrorotatory ones, were firstly described in Italian Patent specification no. 1 203 721, in the Applicant's name. Such Patent, inter alia, states that the levorotatory isomer shows an antitussive action markedly better than the one of dextrorotatory isomer, combined with an activity on central nervous system notably lower than that of the latter isomer, with accordingly decreased side-effects.

Hence, the levorotatory isomer, due to his higher action selectivity, is preferred to the dextrorotatory isomer.

Therefore, a process for the optical resolution of dropopizine, which process is simple, cheap and applicable on industrial scale, is required.

In accordance with the above cited Italian Patent specification no. 1 203 721 levodropropizine can be prepared starting from racemic dropopizine by "conventional means for optical resolution" or can be synthetized starting from optically active 1,2-isopropylidene-sn-glycerol. Nevertheless, whilst the ex novo synthesis method is widely described, no examples for optical resolution of racemic dropopizine are reported. Really, attempts for the optical resolution of the racemate with most of the usual agents for optical resolution failed to succeed.

Especially, trials were performed using the following optically active acids:

| |
|---|
| D(−) tartaric acid |
| D camphosulfonic acid |
| L camphosulfonic acid |
| Camphoric acid |
| D dibenzoyltartaric acid |
| L dibenzoyltartaric acid |
| D toluyltartaric acid |
| L toluyltartaric acid |
| D mandelic acid |
| L mandelic acid |

Now it has been surprisingly found, and it is the object of the invention, that levodropropizine can be separated from racemic mixture in high yields and high purity, using L(+)tartaric acid as agent for optical resolution.

According to the invention, resolution of dropopizine is carried out by treating it with L(+)tartaric acid in aqueous medium: the precipitated salt is then crystallized, alkalinized and recrystallized to give levodropropizine.

Mother liquors containing the partially resolved R(+) isomer are alkalinized and then extracted with methylene cloride. Dropopizine enriched in partially resolved R(+) isomer thus obtained is racemized by mesylation and subsequent substitution of secondary mesyloxy group with an acetoxy or —OH group.

The optimum molar ratio of racemic dropopizine to L(+)tartaric acid is 1:1, nevertheless ratios ranging between 1:0.5 and 1:2 can also be used. The dropopizine/water ratio can range between 1:2 and 1:10.

The process according to the invention is further illustrated by the following examples.

EXAMPLE 1

Resolution of Dropopizine a) Salification

A suspension of dropopizine (500 g) and L(+)tartaric acid (317 g) in water (2.5 l) is heated to dissolution. Any impurity is removed by hot filtering and the clear solution is left to cool to 25°-28° C. and left to stand at this temperature for 24 hours. The precipitated salt is filtered and recrystallized 3 times from water. 150 g of an optically pure salt $[\alpha]_D = -9.4°$ (c =3% in $H_2O$) melting at 195°-7° C. is obtained.

b) Salt shifting

The salt obtained in a) is alkalinized to pH 11 with 10% sodium hydroxide and extracted many times with methylene chloride. The collected organic extracts are dried and evaporated to dryness. The residue, crystallized from acetone, yields 83 g of levodropropizine melting at 102°-104° C. $[\alpha]_D = -24.1°$ (c =3 in $CH_2Cl_2$).

EXAMPLE 2

Racemization of dropopizine rich in R(+) isomer a) Recovery of partially resolved R(+) isomer Mother liquor from salification is alkalinized to pH 11 with 10% sodium hydroxide and repeatedly extracted with methylene chloride. The oganic layers are dried and evaporated to dryness, yielding 280 g of dropopizine rich in R(+) isomer.

b) Racemization of partially resolved R(+) isomer

Mesylchloride (339 g) is slowly added to a solution of partially resolved R(+) isomer (280 g) and triethylamine (300 g) in methylene chloride (3 l). The reaction mixture is stirred for 1 hour, then washed with water. The organic layer is evaporated to dryness and the residue is dissolved in glacial acetic acid (5 l). Acetic anhydride (300 ml), potassium acetate (300 g) are added, and then heated to reflux for 3 hours. Most of the solvent is distilled off and the mixture is diluted with water, alkalinized to pH 10 with 10% sodium hydroxide and extracted 2 times with methylene chloride. The combined organic extracts are dried and evaporated to dryness. The residue is dissolved in 6N hydrochloric acid and the resulting solution is refluxed for 5 hours, then cooled to room temperature and alkalinized to pH 11 with 10% sodium hydroxide. Solution is repeatedly extracted with methylene chloride and the combined organic layers are dried and evaporated to dryness. 200 g of racemic dropopizine is yielded $[\alpha]_D = 0°$ (c =3% in $CH_2Cl_2$).

I claim:

1. A process for the optical resolution of racemic dropropizine, characterized in that it is carried out using L(+)tartaric acid as the optical resolution agent.

2. A process according to claim 1, characterized in that the reaction is carried out in aqueous medium.

3. A process according to claim 1, characterized in that racemic dropropizine/L(+)tartaric acid molar ratio is between 1:0.5 and 1:2.

4. A process according to claim 3, characterized in that racemic dropropizine/L(+)tartaric acid molar ratio is 1:1.

5. A process according to claim 2, characterized in that racemic dropropizine/water molar ratio is between 1:2 and 1:1.

6. A process according to claim 1, characterized in that R(+) isomer present in mother liquor is racemized by treatment with mesyl chloride and acetic anhydride, and in that, after suitable hydrolysis, the thus obtained racemic product is subjected to the treatment according to claim 1.

* * * * *